US006628809B1

(12) United States Patent
Rowe et al.

(10) Patent No.: US 6,628,809 B1
(45) Date of Patent: Sep. 30, 2003

(54) APPARATUS AND METHOD FOR IDENTIFICATION OF INDIVIDUALS BY NEAR-INFRARED SPECTRUM

(75) Inventors: Robert K. Rowe, Corrales, NM (US); William A. Miller, Santa Fe, NM (US); Nanxiang Ge, Newtown, PA (US); Mark Ries Robinson, Albuquerque, NM (US)

(73) Assignee: Lumidigm, Inc., Albuquerque, NM (US)

( * ) Notice: Subject to any disclaimer, the term of this patent is extended or adjusted under 35 U.S.C. 154(b) by 0 days.

(21) Appl. No.: 09/415,594

(22) Filed: Oct. 8, 1999

(51) Int. Cl.[7] .................................................. G06K 9/00
(52) U.S. Cl. ......................... 382/115; 356/71; 340/5.52; 340/5.82; 250/339.02
(58) Field of Search ................................... 382/115, 124, 382/125, 126, 127; 73/73; 250/559.44, 316.1, 339.07, 339.1, 341.8, 339.02; 340/5.52, 5.82; 356/51, 303, 445, 939, 71; 902/3; 707/6; 713/186; 702/19, 76

(56) References Cited

U.S. PATENT DOCUMENTS

| 3,508,830 A | 4/1970 | Hopkins et al. ............ 356/103 |
| 3,910,701 A | 10/1975 | Henderson et al. ........... 356/39 |

(List continued on next page.)

FOREIGN PATENT DOCUMENTS

| EP | 0 280 418 A1 | 8/1988 | ............ A61B/5/00 |
| EP | 0 897 164 A2 | 2/1999 | ............ G07C/9/00 |
| EP | 0 924 656 A2 | 6/1999 | ............ G07C/9/00 |
| WO | WO 92/17765 | 10/1992 | ............ G01N/21/31 |
| WO | WO 93/07801 | 4/1993 | ............ A61B/5/00 |
| WO | WO 01/18332 A1 | 3/2001 | ............ G07C/9/00 |
| WO | WO 01/27882 A2 | 4/2001 | |

OTHER PUBLICATIONS

Nichols, et al., "Design and Testing of a White–light, Steady–state diffuse reflectance spectrometer for Determination of Optical Properties of Highly Scattering Systems"; *Applied Optics*, vol. 36, No. 1, Jan. 1997, pp. 93–104.

Bantle, John P. et al., "Glucose Measurement in Patients with Diabetes Mellitus with Dermal Insterstitial Fluid," copyright © 1997 by Mosby–Year Book, Inc., pp. 436–441.

Bleyer et al., "The costs of Hospitalizations Due to Hemodialysis Access Management", *Nephrology News & Issues*, Jan., 1995, pp. 19, 20 and 22.

Berkoben et al., "Vascular Access for Hemodialysis", *Clinical Dialysis*, published on or before Oct. 30, 1997, 20 pages.

(List continued on next page.)

*Primary Examiner*—Brian Werner
(74) *Attorney, Agent, or Firm*—Townsend and Townsend and Crew LLP

(57) ABSTRACT

Methods and apparatus for non-invasively verifying human identities using near-infrared spectroscopy. Near-infrared tissue spectra can be obtained by projecting near-infrared radiation into skin on the underside of human forearms and capturing the light reflected back and out through the tissue. The tissue spectrum collected preferably includes primarily diffuse reflected light reflected from the inner dermis. Multiple tissue spectra and identities can be collected from individuals for whom identity verification may later be desired. The tissue spectra for each individual can be analyzed on a computer, and the spectra for each individual clustered or classified together using tools such as linear discriminant analysis. A target individual seeking identity verification can submit both a purported identity and a near-infrared tissue spectrum for analysis through near-infrared spectroscopy of the forearm. Similarity between the target spectrum and the multiple spectra for the purported identity in the spectral database is determined and identify verified or not verified based on the degree of similarity.

24 Claims, 6 Drawing Sheets

U.S. PATENT DOCUMENTS

| | | | | |
|---|---|---|---|---|
| RE29,008 E | * | 10/1976 | Ott | 340/172.5 |
| 4,427,889 A | | 1/1984 | Muller | 250/339 |
| 4,653,880 A | | 3/1987 | Sting et al. | 350/620 |
| 4,655,225 A | | 4/1987 | Dahne et al. | 128/633 |
| 4,661,706 A | | 4/1987 | Messerschmidt et al. | 250/341 |
| 4,712,912 A | | 12/1987 | Messerschmidt | 356/73 |
| 4,730,882 A | | 3/1988 | Messerschmidt | 350/96.1 |
| 4,853,542 A | | 8/1989 | Milosevic et al. | 250/353 |
| 4,859,064 A | | 8/1989 | Messerschmidt et al. | 356/446 |
| 4,882,492 A | | 11/1989 | Schlager | 250/346 |
| 4,944,021 A | * | 7/1990 | Hoshino et al. | 382/5 |
| 4,975,581 A | * | 12/1990 | Robinson et al. | 250/339 |
| 5,015,100 A | | 5/1991 | Doyle | 356/445 |
| 5,019,715 A | | 5/1991 | Sting et al. | 250/571 |
| 5,028,787 A | | 7/1991 | Rosenthal et al. | 250/341 |
| 5,051,602 A | | 9/1991 | Sting et al. | 250/571 |
| 5,070,874 A | | 12/1991 | Barnes et al. | 128/633 |
| 5,158,082 A | | 10/1992 | Jones | 128/633 |
| 5,163,094 A | * | 11/1992 | Prokoski et al. | 382/2 |
| 5,179,951 A | | 1/1993 | Knudson | 128/633 |
| 5,222,495 A | | 6/1993 | Clarke et al. | 128/633 |
| 5,222,496 A | | 6/1993 | Clarke et al. | 128/633 |
| 5,225,678 A | | 7/1993 | Messerschmidt | 250/339 |
| 5,230,702 A | | 7/1993 | Lindsay et al. | 604/4 |
| 5,237,178 A | | 8/1993 | Rosenthal et al. | 250/341 |
| 5,257,086 A | | 10/1993 | Fateley et al. | 356/328 |
| 5,299,570 A | | 4/1994 | Hatschek | 128/633 |
| 5,311,021 A | | 5/1994 | Messerschmidt | 250/339.01 |
| 5,321,265 A | | 6/1994 | Block | 250/343 |
| 5,331,958 A | | 7/1994 | Oppenheimer | 128/633 |
| 5,348,003 A | | 9/1994 | Caro | 128/633 |
| 5,351,686 A | | 10/1994 | Steuer et al. | 128/633 |
| 5,355,880 A | | 10/1994 | Thomas et al. | 128/633 |
| 5,366,903 A | | 11/1994 | Lundsgaard et al. | 436/165 |
| 5,372,135 A | | 12/1994 | Mendelson et al. | 128/633 |
| 5,379,764 A | | 1/1995 | Barnes et al. | 128/633 |
| 5,402,778 A | | 4/1995 | Chance | 128/633 |
| 5,405,315 A | | 4/1995 | Khuri et al. | 128/633 |
| 5,435,309 A | | 7/1995 | Thomas et al. | 128/663 |
| 5,452,723 A | | 9/1995 | Wu et al. | 128/664 |
| 5,494,032 A | | 2/1996 | Robinson et al. | 128/633 |
| 5,505,726 A | | 4/1996 | Meserol | 606/9 |
| 5,507,723 A | | 4/1996 | Keshaviah | 604/5 |
| 5,518,623 A | | 5/1996 | Keshaviah et al. | 210/646 |
| 5,533,509 A | | 7/1996 | Koashi et al. | 128/633 |
| 5,539,207 A | | 7/1996 | Wong | 250/339.08 |
| 5,559,504 A | * | 9/1996 | Itsumi et al. | 340/825.3 |
| 5,630,413 A | | 5/1997 | Thomas et al. | 128/633 |
| 5,636,633 A | | 6/1997 | Messerschmidt et al. | 128/633 |
| 5,655,530 A | * | 8/1997 | Messerschmidt | 128/633 |
| 5,681,273 A | | 10/1997 | Brown | 604/6 |
| 5,719,950 A | | 2/1998 | Osten et al. | 382/115 |
| 5,737,439 A | | 4/1998 | Lapsley et al. | 382/115 |
| 5,751,835 A | | 5/1998 | Topping et al. | 382/115 |
| 5,761,330 A | * | 6/1998 | Stoianov et al. | 382/127 |
| 5,792,050 A | | 8/1998 | Alam et al. | 600/310 |
| 5,793,881 A | | 8/1998 | Stiver et al. | 382/115 |
| 5,823,951 A | | 10/1998 | Messerschmidt et al. | 600/322 |
| 5,830,132 A | | 11/1998 | Robinson | 600/310 |
| 5,857,462 A | | 1/1999 | Thomas et al. | 128/633 |
| 5,867,265 A | * | 2/1999 | Thomas | 356/328 |
| 5,935,062 A | | 8/1999 | Messerschmidt et al. | 600/322 |
| 5,987,346 A | | 11/1999 | Benaron et al. | 600/407 |
| 5,999,637 A | * | 12/1999 | Toyoda et al. | 382/124 |
| 6,041,410 A | | 3/2000 | Hsu et al. | 713/186 |
| 6,069,689 A | | 5/2000 | Zeng et al. | 356/73 |
| 6,088,607 A | | 7/2000 | Diab et al. | 600/322 |
| 6,115,484 A | | 9/2000 | Bowker et al. | 382/127 |
| 6,122,042 A | * | 9/2000 | Wunderman et al. | 356/73 |
| 6,122,394 A | | 9/2000 | Neukermans et al. | 382/124 |
| 6,148,094 A | | 11/2000 | Kinsella | 382/124 |
| 6,152,876 A | | 11/2000 | Robinson et al. | 600/322 |
| 6,154,658 A | * | 11/2000 | Caci | 455/466 |
| 6,157,041 A | | 12/2000 | Thomas et al. | 250/573 |
| 6,159,147 A | | 12/2000 | Lichter et al. | 600/300 |
| 6,172,743 B1 | | 1/2001 | Kley et al. | 356/39 |
| 6,181,414 B1 | | 1/2001 | Raz et al. | 356/51 |
| 6,181,958 B1 | | 1/2001 | Steuer et al. | 600/322 |
| 6,240,309 B1 | | 5/2001 | Yamashita et al. | 600/407 |
| 6,256,523 B1 | | 7/2001 | Diab et al. | 600/323 |
| 6,272,367 B1 | | 8/2001 | Chance | 600/407 |
| 6,280,381 B1 | | 8/2001 | Malin et al. | 600/322 |
| 6,285,895 B1 | | 9/2001 | Ristolainen et al. | 600/323 |
| 6,301,815 B1 | | 10/2001 | Sliwa | 42/70.1 |
| 6,304,767 B1 | | 10/2001 | Soller et al. | 600/322 |
| 6,307,633 B1 | | 10/2001 | Mandella et al. | 356/479 |
| 6,309,884 B1 | | 10/2001 | Cooper et al. | 436/413 |
| 6,317,507 B1 | * | 11/2001 | Dolfing | 382/119 |
| 6,330,346 B1 | * | 12/2001 | Peterson et al. | 382/115 |

OTHER PUBLICATIONS

Daugirdas et al., "Comparison of Methods to Predict the Equilibrated Kt/V (eKt/V) in the Hemo Study", National Institutes of Health, NIDDK, Bethesda, MD, Aug. 20, 1996.

Depner et al., "Clinical Measurement of Blood Flow in Hemodialysis Access Fistulae and Grafts by Ultrasound Dilution", from the Department of Nephrology, University of California, published bon or before Oct. 30, 1997, 4 pages.

Jacobs et al., "A Disposable Urea Sensor for Continuous Monitoring of Hemodialysis Efficiency", USAIO Journal, 1993, pp. M353–M358.

Hakim et al., "Effects of Dose of Dialysis on Morbidity and Mortality", *American Journal of Kidney Diseases*, vol. 23, No. 5, May 1994, pp. 661–669.

Keshaviah et al., "On–line monitoring of the delivery of the hemodialysis prescription", *Pediatric Nephrology*, vol. 9, 1995, pp. S2–S8.

Krivitski, "Theory and Validation of Access Flow Measurement by Dilution Technique During Hemodialysis", *Kidney International*, vol. 48, 1995, pp. 244–250.

Marbach, "Measurement Techniques for IR Spectroscopic Blood Glucose Determination", 1993.

Mardia, K. V. et al., *Multivariate Analysis*, Academic Press (1979) pp. 300–325.

Ripley, B. D. *Pattern Recognition and Neural Networks*, Cambridge University Press (1996) pp. 91–120.

Ronco et al., "On–line urea monitoring: a further step towards adequate dialysis prescription and delivery", *Int'l. Journal of Artificial Organs*, vol. 18, No. 9, 1995, pp. 534–543.

Service, F. John et al., Dermal Interstitial Glucose as an Indicator of Ambient Glycemia, *Diabetes Care*, vol. 20, No. 9, Sep. 1997, 9 pages.

Sherman, "Recirculation in the Hemodialysis Access", *Principles and Practice of Dialysis*, published on or before Oct. 30, 1997, 9 pages.

Sherman, "The Measurement of Dialysis Access Recirculation", *American Journal of Kidney Diseases*, vol. 22, No. 4, Oct. 1993, pp. 616–621.

Steuer et al., "A New Optical Technique for Monitoring Hematocrit and Circulating Blood Volume: Its Application in Renal Dialysis", *Dialysis & Transplantation*, vol. 22, No. 5, May 1993, 5 pages.

Webb, Paul, "Temperatures of Skin, Subcutaneous Tissue, Muscle and Core in Resting Men in Cold, Comfortable and Hot Conditions," *European Journal of Applied Physiology*, vol. 64 (1992) pp. 471–476.

Brochure entitled "Determination of Delivered Therapy Through Measurement of Effective Clearance", Feresenius USA, Dec. 1994, 1 page.

Brochure entitled "Improve the Clinical Outcome of Every Patient", In Line Diagnostics, published on or before Oct. 30, 1997, 2 pages.

* cited by examiner

APPARATUS AND METHOD FOR IDENTIFICATION OF INDIVIDUALS BY NEAR-INFRARED SPECTRUM

CROSS REFERENCE TO RELATED PATENTS AND PENDING APPLICATIONS

The present application is related to U.S. Pat. No. 6,152,876, filed Oct. 19, 1998, entitled "Method for Non-Invasive Analyte Measurement with Improved Optical Interface", and U.S. Pat. No. 5,935,062, filed Jun. 9, 1997, entitled "Diffuse Reflectance Monitoring Apparatus", both assigned to the same assignee as the present application.

TECHNICAL FIELD

The present invention relates generally to methods and systems for verifying the identity of an individual utilizing spectral data from a non-invasive near-infrared tissue analysis. More specifically, the invention relates to non-invasive methods and apparatus for verifying identity of a living individual using near-infrared absorption of light energy by tissue with identity verified using multivariate discriminant analysis techniques on resulting subcutaneous tissue spectral data as compared to prior stored spectral data for that individual.

BACKGROUND OF THE INVENTION

Identity verification is useful in many applications. Examples include verifying identity prior to activating machinery or gaining entry to a secure area. Another example would be identity verification of an individual for matching that individual to records on file for that individual, such as for matching hospital patient records when the individual's identity is unknown. Identity verification is also useful to match police records at the time a suspect is apprehended, but true identity of the suspect is not known. Passwords, keys, numeric codes and fingerprints are solutions currently in use. However, keys and codes can be used by anyone having possession of the keys or codes. A requirement that the person physically at a site be the person authorized to use the key or password is not easily enforced. Fingerprint analysis generally fails to give instant results and security systems relying on fingerprint analysis can be circumvented, as disclosed by Osten et al. in U.S. Pat. No. 5,719,950.

Living human tissue is recognized as a dynamic system containing a multitude of components and analyte information that is particularly useful in the medical profession for diagnosing, treating and monitoring human physical conditions. To this end, effort has been directed toward developing methods for non-invasive measurement of tissue constituents using spectroscopy. The spectrographic analysis of living tissue has been focused on the identification of spectral information that defines individual analytes and relates such spectral data to the analyte's concentration. Concentrations of these analytes vary with time in an individual patient. Acquiring tissue spectral data with sufficient accuracy for use in diagnosis and treatment has proven difficult. Difficulties in conducting the analysis have been found which are related to the fact that the tissue system is a complex matrix of materials with differing refractive indices and absorption properties. Further, because the constituents of interest are many times present at very low concentrations, high concentration constituents, such as water, have had a detrimental impact on identifying the low level constituent spectral information and giving an accurate reading of the desired constituent concentration. Development of these techniques has always focused on the changes in spectral output with change in concentration of a dynamic analyte of interest, such as glucose. The techniques disclosed are focused on identifying concentrations of specific analytes, the concentration of which is expected to vary with time.

Improved methods and apparatus for gathering and analyzing a near-infrared tissue spectrum for an analyte concentration are disclosed in commonly assigned U.S. patent applications and issued patents. U.S. Pat. No. 5,655,530 and U.S. Pat. No. 5,823,951, filed Apr. 18, 1997, entitled "Method for Non-invasive Blood Analyte Measurement with Improved Optical Interface" relate to near-infrared analysis of a tissue analyte concentration which varies with time, with a primary focus on glucose concentrations in diabetic individuals. The methods and apparatus include placing a refractive index-matching medium between a sensor and the skin to improve the accuracy and repeatability of testing. U.S. Pat. No. 6,152,876, filed Oct. 19, 1998, entitled "Method for Non-Invasive Blood Analyte Measurement with Improved Optical Interface" discloses additional improvements in non-invasive living tissue analyte analysis. The disclosure of each of these three applications or patents are hereby incorporated by reference.

U.S. Pat. No. 5,636,633 relates, in part, to another aspect of accurate non-invasive measurement of an analyte concentration. The apparatus includes a device having transparent and reflective quadrants for separating diffuse reflected light from specular reflected light. Incident light projected into the skin results in specular and diffuse reflected light coming back from the skin. Specular reflected light has little or no useful information and is preferably removed prior to collection. U.S. Pat. No. 5,935,062, filed Jun. 9, 1997, entitled "Improved Diffuse Reflectance Monitoring Apparatus", discloses a further improvement for accurate analyte concentration analysis which includes a blocking blade device for separating diffuse reflected light from specular reflected light. The blade allows light from the deeper, inner dermis layer to be captured, rejecting light from the surface, epidermis layer, where the epidermis layer has much less analyte information than the inner dermis layer, and contributes noise. The blade traps specular reflections as well as diffuse reflections from the epidermis. The disclosures of the above patent and application, which are assigned to the assignee of the present application, are also incorporated herein by reference.

U.S. Pat. No. 5,435,309 relates to a system for selecting optimal wavelengths for multivariate spectral analysis. The use of only one wavelength gives insufficient information, especially for solutions having multiple components. The use of too many wavelengths can include too much noise and lead to combinatorial explosion in calculations. Therefore, the number of wavelengths used should be limited and the wavelengths well chosen. Genetic algorithms are used in this reference to select the most fit wavelengths. The disclosure of this patent is incorporated herein by reference.

SUMMARY OF THE INVENTION

In contrast to the above discussed prior art techniques for non-invasive analysis of a blood or tissue analyte concentration using infrared spectroscopy, the present invention is based on applicant's recognition that the resultant tissue spectrum of a particular individual includes unique spectral features and combinations of spectral features which can be used to identify the individual once the analytical device has been trained to identify the individual. Spectral information in the near infrared range is preferred, however, it is recognized that visible or mid-infrared light energy could be used alone or in combination with near infrared. Training of the device is accomplished by use of stored spectral data for that individual from prior testing. Applicants have been able to achieve essentially zero percent false positive error rates with the techniques disclosed herein, even though the tissue being analyzed is a dynamic system with analyte concentrations, and thus, tissue spectral data, varying considerably over time and between analysis. Success of the method of the present invention is believed tied to two components. First, the method incorporates an apparatus and technique for accurately and repeatably acquiring a tissue spectrum which is stable, while remaining sensitive to slight changes in spectral output at any given wave length. The system optimizes optical throughput both into and out of the tissue sample. Second, because the spectral features or combinations of spectral features that are unique for a particular individual are not readily apparent or identified by visual comparison of a spectral result, the present invention relies on discriminant analysis techniques to first train the device to identify spectral features of significance for the individual and then compare such features to new spectral data at the time of attempted verification. The method can incorporate a discriminant analysis technique based upon Mahalanobis distance technique or other distance techniques to compare spectral data acquired from an individual with spectral data present in a database.

The present invention, thus, includes a method for verifying the identity of an individual using non-invasive tissue spectroscopy. A preferred method and apparatus illuminates skin with near-infrared radiation and collects the reflected, non-absorbed near-infrared radiation. Diffuse, rather than specular, reflected light is preferably collected, more preferably light diffusely reflected from the inner dermis rather than the epidermis. The near-infrared spectral data collected can be stored in a computer database. A series of such spectral data are collected from the individual or individuals for which identity verification is desired. The identity of the individual is preferably verified and stored along with the associated spectral data in an authorization database. Authorized spectra can be collected over a period of minutes, or more preferably, a number of spectra can be collected over days and weeks, which allows for adjustment of the individual's model for verification to account for natural physiological differences at any given time of analysis which will affect a person's tissue spectra.

After collection, the authorization spectral database for a particular individual can be analyzed, using discriminant analysis tools, relative to new spectral data from an individual purporting to be that individual or an unknown individual. When the purported identity of a target individual is to be verified or an unknown individual's identity is to be checked against a stored database, a target tissue spectrum can be taken and processed in a manner similar to the processing of the already stored authorization spectra. In one method, the Mahalanobis distance and spectral residual magnitude are used to verify the purported identity or check the unknown individual's spectral data against a database. In a preferred method, the Mahalanobis distance and spectral residual magnitude are calculated for the target spectrum relative to the database spectra for the individual with the purported identity. Identify is verified only if the aforementioned distance and magnitude are less than a predetermined threshold set for each.

One system for performing identity verification includes: a computer having an input device and an output device; a database including near-infrared tissue spectral data for authorized persons or a collection of spectral data for individuals against which unknown individual's would be checked; a near-infrared radiation source for projecting near-infrared radiation into subcutaneous tissue; a near-infrared spectrometer for measuring subcutaneous near-infrared intensity over a plurality of wavelengths; and a program running in the computer for discriminating between a target individual's spectral data and the authorized spectral data or collection of spectra database containing spectra for a group of individuals. The program can include software for performing discriminant analysis. In one system, supervised learning programs can be utilized to assist in associating the various spectral data for each identified individual together.

These and various other advantages and features of novelty which characterize the present invention are pointed out with particularity in the claims annexed hereto and forming a part hereof. However, for a better understanding of the invention, its advantages, and the object obtained by its use, reference should be made to the drawings which form a further part hereof, and to the accompanying descriptive matter in which there are illustrated and described preferred embodiments of the present invention.

BRIEF DESCRIPTION OF THE DRAWINGS

In the drawings, in which like reference numerals indicate corresponding parts or elements of preferred embodiments of the present invention throughout the several views.

DETAILED DESCRIPTION OF THE PREFERRED EMBODIMENTS

Figure 1:
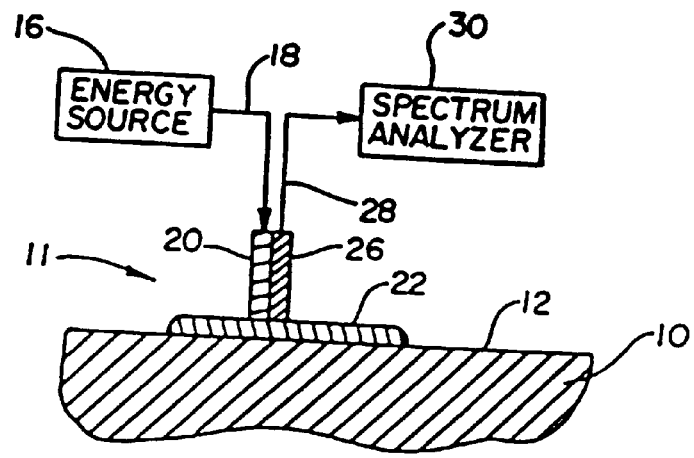
FIG. 1 is a partial cross-sectional view of a sensor element coupled to the skin surface via an indexing-matching fluid.

Detailed embodiments of the present invention are disclosed herein. However, it is to be understood that the disclosed embodiments are merely exemplary of the present invention which may be embodied in various systems. Therefore, specific details disclosed herein are not to be interpreted as limiting, but rather as a basis for the claims and as a representative basis for teaching one of skill in the art to variously practice the invention.

The present invention is based on Applicant's recognition that an accurate, precise and repeatable tissue spectra of an individual in the near infrared range contains spectral features and combinations of spectral features which are unique to that individual. It is further believed that some unique information may be present in the visible light region, with the techniques disclosed herein adaptable to such analysis. The present invention is further based on a recognition that proper analysis, utilizing discriminant analysis techniques, can identify these unique features or combinations, which are not readily apparent in visual analysis of a spectral output, so that an individual's identity may be verified by comparison of a tissue spectral data taken at the time of verification compared to stored tissue spectral data from prior testing. The identification methods can also be used in conjunction, or simultaneously, with measurement of analyte concentrations in an individual.

The prior spectral data is used to train the device to identify that particular person based on features that are recognized unique to that particular individual. These unique spectral features have been found to be consistently present even though the tissue being analyzed at each time of analysis is a dynamic system which contains components and analytes whose concentration vary, with resulting tissue spectral variations, due to physiological changes in the individual.

As previously stated, there are two components to the success of the method of the present invention. First, the method incorporates an apparatus and technique to accurately and repeatably acquire tissue spectral data. The apparatus is sensitive to slight changes in spectral output at any given wavelength of input and optimizes the overall optical throughput both into and out of the tissue sample. Second, the method requires specific techniques for training the instrument to identify spectral features of significance for that particular individual, and then to compare such features to a new spectral data acquired at the time of attempted verification. Because the spectral features or combinations of spectral features that are unique for a particular individual are not readily apparent or identified by visual comparison of a spectral result and the unique spectral features are present at different wavelengths for different individuals, the present invention relies on discriminant analysis techniques to compare spectral data. Each component of the apparatus and method of the present invention are detailed below.

The present invention utilizes an accurate, repeatable and sensitive method for non-invasive measurement of a near infrared tissue spectral data. It is recognized that the sample is a complex matrix of materials with differing refractive indices and absorption properties. Further, because many constituents are present at very low concentrations, it has been found to be imperative to couple light into and out from the tissue in an efficient manner. The method of the present invention incorporates an index-matching medium, fluid or deformable solid, to improve the efficiency of coupling the light both into and out of the tissue sample.

The present invention utilizes light energy in the near-infrared region of the optical spectrum as an energy source for analysis. Water is by far the largest contributor to absorption in tissue in the near-infrared region because of its concentration, as well as its strong absorption coefficient. It has been found that the total absorption spectrum of tissue, therefore, closely resembles the water spectrum. Less than 0.1 percent of the absorption of light is from, for instance, a constituent such as glucose. It has been further found that tissue greatly scatters light because there are many refractive index discontinuities in a typical tissue sample. Water is perfused through the tissue, with a refractive index of 1.33. Cell walls and other features of tissue have refractive indices closer to 1.5 to 1.6. These refractive index discontinuities give rise to scatter. Although these refractive index discontinuities are frequent, they are also typically small in magnitude and the scatter generally has a strong directionality towards the forward direction.

This forward scatter has been described in terms of anisotropy, which is defined as the cosine of the average scatter angle. Thus, for complete backwards scatter, meaning that all scatter events would cause a photon to divert its direction of travel by 180 degrees, the anisotropy factor is −1. Likewise, for complete forward scatter, the anisotropy factor is +1. In the near infrared, tissue has been found to have an anisotropy factor of around 0.9 to 0.95, which is very forward scattering. For instance, an anisotropy factor of 0.9 means that an average photon of light only scatters through an angle of up to 25 degrees as it passes through the sample.

In acquiring tissue spectral data, measurements can be made in at least two different modes. It is recognized that one can measure light transmitted through a section of tissue, or one may measure light reflected or remitted from tissue. It has been recognized that transmission is the preferred method of analysis in spectroscopy because of the forward scattering of light as it passes through the tissue. However, it is difficult to find a part of the body which is optically thin enough to pass near infrared light through, especially at the longer wave lengths. Thus, the preferred method for measurement in the present invention is to focus on the reflectance of light from the sample.

Photons reflect and refract at refractive index discontinuities, and so light impinging on tissue immediately has a small reflectance at the tissue surface. This is referred to as specular reflectance. Since this light does not penetrate into the tissue, it contains little information about the tissue constituents. This is especially true in light of the physiology of skin, which possesses an outward layer which is essentially dead and lacks spectral information believed unique to an individual. Thus, reflected light energy containing spectral data unique to an individual is believed to be that light which is reflected back to the surface through refractive index discontinuities deeper within the tissue sample. This reflected light energy is referred to as diffusely reflected light.

Applicants have found that a large fraction of incident photons are absorbed and scattered in the tissue. Those photons which are available for coupling back out of the tissue are likely diverted in their angular path. In fact, by definition, a photon must change direction in order to exit the tissue in a direction towards the input optic. Applicants, however, have found that a large problem with detection is associated with the refractive index discontinuity between the average tissue refractive index and the refractive index of air outside of the tissue. It has been found that this discontinuity acting on incident light leads to a refraction and a small specular reflectance of less than about 5 percent. However, on the way out, the discontinuity gives rise to a critical angle phenomenon. Because the photon is traveling from a high refractive index medium to a lower one, a critical angle exists above which a photon is totally internally reflected and will not escape the tissue sample. This critical angle for photons traveling from tissue to air has been found to be about 46 degrees, which presents a problem. A photon normally incident on the tissue surface must deviate through a large angle to exit. Because of the forward directionality of scattering, this is difficult for a photon to do, and it is very likely to make a grazing or high angle incidence with the tissue and air interface. The grazing incidence photons will not escape because the critical angle is exceeded.

Applicants have found a solution for the differences in refractive index associated with coupling light energy exiting tissue to an analytical instrument. The solution is the use of an immersion fluid which has very low absorptivity in the spectral range of interest, and has a viscosity compatible with good flow and coverage, while having a refractive index which effectively introduces light into the tissues, reduces specular reflection and effectively gets light back out of the tissue. In preferred embodiments, the index-matching fluid is preferably minimally or essentially non-absorbing of light energy in the wavelengths selected as relevant to identification of an individual. The fluid is thus non-spectroscopically active at desired wavelengths. However, it is believed a minimally absorbing index-matching fluid, for example one that absorbs less than about 10% of the light energy of relevant wavelengths, could still be utilized. A preferred material is a fluorinated, chlorinated hydrocarbon polymer oil manufactured by Occidental Chemical under the tradename FLUOROLUBE. FS5 is a preferred FLUOROLUBE. These oils have a refractive index of about 1.38, are non-toxic, and Applicants have found that it has a spectral signature in the near infrared region which is minimal.

Figure 2:
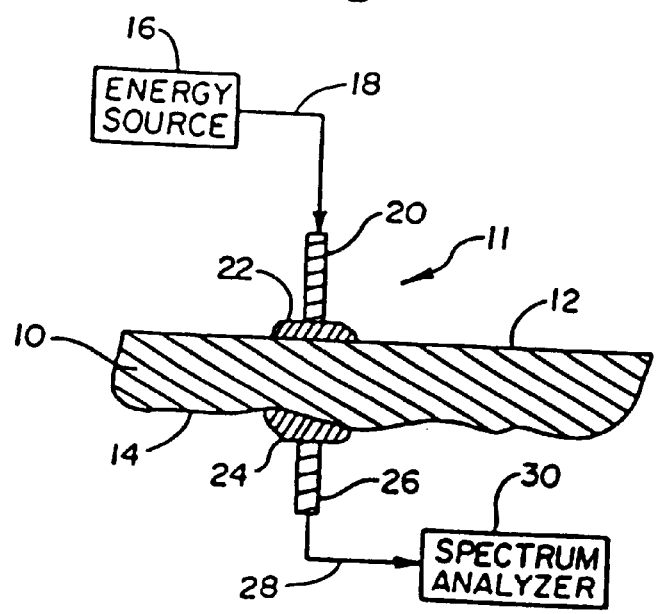
FIG. 2 is a partial cross-sectional view of an alternative embodiment of a sensor element coupled to opposite sides of a skin surface via an indexing-matching fluid.

Now referring to FIGS. 1 and 2, partial cross-sectional views of two preferred embodiments of an apparatus for non-invasively acquiring a tissue spectrum are depicted. The depictions in FIGS. 1 and 2 are schematic to depict the concept of utilizing an index-matching medium 22 in conjunction with a non-invasive sensor element 11 operatively connected to an energy source 16 and a spectrum analyzer 30. The relative size, shape and detail of physical components are not depicted.

The apparatus depicted in FIG. 1 and the apparatus depicted in FIG. 2 generally include three elements, an energy source 16, a sensor element 11, and a spectrum analyzer 30. The embodiment of FIG. 1 depicts the sensor element as including an input element 20 and an output element 26, which can include a single lens system for both input and output light energy. The input element 20 and output element 26 are in contact with a common skin surface 12 of the selected tissue 10. The alternative embodiment of is FIG. 2 depicts an alternative sensor element 11 arrangement, wherein the input element 20 and output element 26 are arranged on opposing surfaces 12, 14 of tissue 10. Both embodiments function to give a measure of the absorption of infrared energy by the tissue 10. However, the embodiment of FIG. 1 is utilized to measure the quantity of light energy which is reflected from the tissue 10 by the components or features therein. In contrast, the embodiment of FIG. 2 measures the transmission of light energy through the tissue 10. In either embodiment, the absorption at various wavelengths can be determined by comparison to the intensity of the light energy from the energy source 16.

The energy source 16 is preferably a wide band, infrared black body source. The optical wavelengths emitted from the energy source 16 are preferably between 1.0 and 2.5 $\mu$m. The energy source 16 is operatively coupled to a first means for transmitting infrared energy 18 from the energy source to the input element 20. In preferred embodiments, this first means 18 is simply the transmission of light energy to the input element 20 through air by placing the energy source 16 proximate the input element 20.

The input element 20 of the sensor element 11 is preferably an optical lens which focuses the light energy to a high energy density spot. However, it is understood that other beam focusing means may be utilized in conjunction with the optical lens to alter the area of illumination. For example, a multiple lens system, tapered fibers, or other conventional optical beam-shaping devices could be utilized to alter the input light energy.

In both embodiments depicted in FIGS. 1 and 2, an output sensor 26 is utilized to receive reflected or transmitted light energy from the tissue 10. In a preferred embodiment, a specular control device is incorporated to separate the specular reflected light from diffusely reflected light. Such devices are disclosed in co-pending and commonly assigned U.S. Pat. No. 5,935,062, filed Jun. 9, 1997, and entitled "Diffuse Reflectance Monitoring Apparatus", the disclosure of which is incorporated herein by reference. As described in conjunction with a method of analysis below, the embodiment of FIG. 1 has an output sensor 26 which receives reflected light energy, while the embodiment of FIG. 2 includes an output sensor 26 which receives transmitted light through the tissue 10. As with the input element 20, the output element 26 is preferably an optical lens. Other optical collection means may be incorporated into an output element 26, such as a multiple lens system, tapered fiber, or other beam-collection means to assist in directing the light energy to the spectrum analyzer 30.

A second means for transmitting infrared energy 28 is operatively connected to the output element 26. The light transmitted through the second means for transmitting infrared energy 28 is transmitted to the spectrum analyzer 30. In a preferred embodiment, the operative connection to the output element includes transmission of the reflected or transmitted light energy exiting the output element through air to the spectrum analyzer 30. A mirror or series of mirrors may be utilized to direct this light energy to the spectrum analyzer.

In practicing the method of the present invention, tissue 10 area is selected as the point of analysis. This area can include the skin surface 12 on the finger, earlobe, forearm, or any other skin surface. Preferably, the area for sampling includes blood vessels near the surface, and a relatively smooth, uncalloused surface. A preferred sample location is the underside of the forearm. A quantity of an index-matching medium 22, whether fluid or deformable solid, is then placed on the skin surface 12 in the area to be analyzed to couple the sensor element 11, which includes the input element 20 and the output element 26 to the instrument.

In acquiring spectral data of the tissue 10, light energy from the energy source 16 is transmitted through the first means for transmitting infrared energy 18 into the input element 20. The light energy is transmitted from the input element 20 through the index-matching medium 22, to the skin surface 12. The light energy contacting the skin surface 12 is differentially absorbed by the various components and analytes contained below the skin surface 12. In a preferred embodiment, the non-absorbed light energy is reflected back to the output element 26 upon propagating again through the index-matching medium 22. The non-absorbed light energy is transmitted via the second means for transmitting infrared energy 28 to the spectrum analyzer 30.

In the alternative embodiment of FIG. 2, the light energy propagated through the input element 20 and first quantity of index-matching medium 22 is differentially absorbed by the tissue 10, while a quantity of the light energy at various wavelengths is transmitted through the tissue 10 to the opposing or second skin surface 14. From the second skin surface 14, the non-absorbed light energy is propagated through the second quantity of index-matching medium 24 to the output element 26 with subsequent propagation to the spectrum analyzer 30 for producing the tissue spectrum.

As previously stated, the index-matching medium 22 of the present invention is a key to the improved accuracy and repeatability of the method described above. The index-matching medium can preferably be a fluid composition containing chlorofluorocarbons. The composition can also be a mixture of chlorofluorocarbons and perfluorocarbons. A preferred composition includes chlorotrifluoroethylene. A preferred composition contains about 80% to about 99.8% by weight of chlorofluorocarbons. As previously stated, the present invention utilizes an index-matching fluid to optimize the input and output of light energy to and from a tissue to be analyzed. In its broadest sense, the index-matching fluid of the present invention can be any fluid which creates an improved optical interface over that interface which results from simply placing the probe of the present invention on a skin surface. Absent the index-matching fluid of the present invention, this interface can include gaps which are air filled and cause detrimental refraction of light both going into the tissue and exiting the tissue. Thus, any index-matching fluid having a refractive index closer to that of the tissue at about 1.38 versus the refractive index of air of about 1.0 would provide an improved interface.

An optimum system includes an index-matching fluid which effectively introduces light into the tissue, reduces specular reflection, and effectively gets light back out of the tissue. The selection of the refractive index for the fluid must be optimized by a taking into account the refractive index of the tissue and the lens system. The process of maximizing the throughput of the system from an index-matched perspective is governed by the equation:

$$N_2 = \sqrt{N_1 \cdot N_3}$$ Equation 1

Where $N_1$ is the refractive index of the tissue, $N_3$ is the refractive index of the optical system and $N_2$ is the refractive index of the optical coupling medium. Although a wide range of matching fluid indexes can be used with little percentage change in overall transmission into the tissue, a key is the amount of back reflected light which contributes to unwanted specular light. With the above controlling equation, in a system with a tissue index of 1.38 and a lens index of 1.42, the ideal matching fluid index is 1.39986. Using this as a reference, the amount of light reflected front the interface will double if the fluid value of 1.38 or 1.42 is utilized.

It has been found that minimization of specular light via appropriate index matching is critical due to the fact that specular artifacts are difficult to model with conventional spectrographic modeling tools. Specular light is additive in intensity units, but non-linear in absorbance units. As partial least squares analysis is conducted in absorbance space, such non-linearities are detrimental to the analysis due to the fact that a partial least squares analysis is a linear model.

Applicants have also recognized that the usefulness of the apparatus of the present invention requires that the coupling of the sensor be repeatable and that the results be an accurate reflection of the tissue constituents of the patient. To this end, Applicants have found that it is preferable for the index-matching fluids of the present invention to contain diagnostic additives and/or physiological additives. The diagnostic additives provide an assessment of the quality of the lens to tissue interface and/or an assessment of the instrument's present performance, while the physiological additives alter the physiology of the tissue to correct for differences in tissue analyte concentration versus blood analyte concentration. A discussion of these additives follows.

The non-invasive measurement of tissue spectral data by the present invention is improved by placing an additive into the index-matching fluid that allows evaluation of the thickness of the fluid when the tissue is placed in contact with the instrument. In preferred embodiments, the additive also provides a calibration of the instrument by including a compound of known high absorption at a specified wavelength of light. Such additives also further assure that the correct index-matching fluid is being utilized for the instrument.

Since an index-matching fluid inherently causes a change of height in the tissue above the sample probe, the measurement of this height can aid in the overall glucose or other analyte measurement, while allowing a path length correction to be applied to the spectral measurement as a function of the tissue height above the sampler. This can insure a reproducible, consistent height is achieved before commencing the spectral measurement of the tissue, and further allows for the adjustment of the height before commencing the spectral measurement of the tissue. In this way, the user can be certain that spurious results are not achieved due to excess matching fluid height, insufficient index-matching fluid being utilized, or some other misplacement of the tissue surface relative to the analyzer.

Laboratory spectrometers utilize a Fourier Transform system which incorporates a laser reference signal to establish the wavelengths and guarantees that the instrument is calibrated. However, it is likely, instruments that are affordable for an end user will not use a laser, but rather will be dispersion type instruments such as gratings, CCD arrays and others. With such instruments, it is important to make certain that calibration is proper prior to each analysis of tissue spectral data. To this end, Applicants have found that the addition of an additive which includes a well-defined spectral feature at a known wavelength of light can be utilized to assure calibration.

The use of a known spectrally active additive to the index-matching fluid also insures that the end user is using a correct index-matching fluid for which the instrument has been calibrated and programmed. The use of a different index-matching fluid could result in an error in the non-invasive tissue spectrum by absorbing light energy in the areas of interest for identifying an individual.

To accomplish the above repeatability, accuracy and quality assurance, a spectroscopically active agent is preferably added to the index-matching fluid. The agent preferably has sharp bands of absorption outside the region of interest to be measured. For example, in a preferred method for identification of individuals, the agent would be active outside the range of 4200 to 7200 wave numbers. The agent could also be active within this range so long as there is no significant overlap with wavelengths actually used to verify an individual's identity. The additive can be manufactured by placing an appropriate functional group on perfluorinated hydrocarbons. The perfluorinated hydrocarbons are spectrally inactive in the region of interest, however, the functional group placed upon the perfluorinated hydrocarbons may be spectrally active. Further, these functional groups do not interfere with the analysis of the blood analyte of interest. Exemplary compounds include perfluoro-2-butyltetrahydrofuran and perfluorosuccinyl chloride.

In an alternative embodiment, the index-matching fluid and diagnostic additive can comprise the same fluid which provides both functions. For example, perfluoro-2-butyltetrahydrofuran can be utilized as an index-matching medium which improves the optical interface, and at the same time includes a functional group which makes the compound spectrographically active in a desired range for diagnostic purposes.

Applicants believe that vasodilating agents which are topically applied can be used in conjunction with the present analysis. These agents can be incorporated into the index-matching medium. These agents work by diffusing into the skin and blocking the adrenergic receptors on the small arterioles that feed the capillary vessels. This results in dilation of the arterial sphincters, a reduction of resistance to flow, and an increase in pressure and size of the capillaries. A number of preferred vasodilating agents include: methyl nicotinamide, minoxidil, nitroglycerin, histamine, menthol, and capsaicin.

Figure 3:
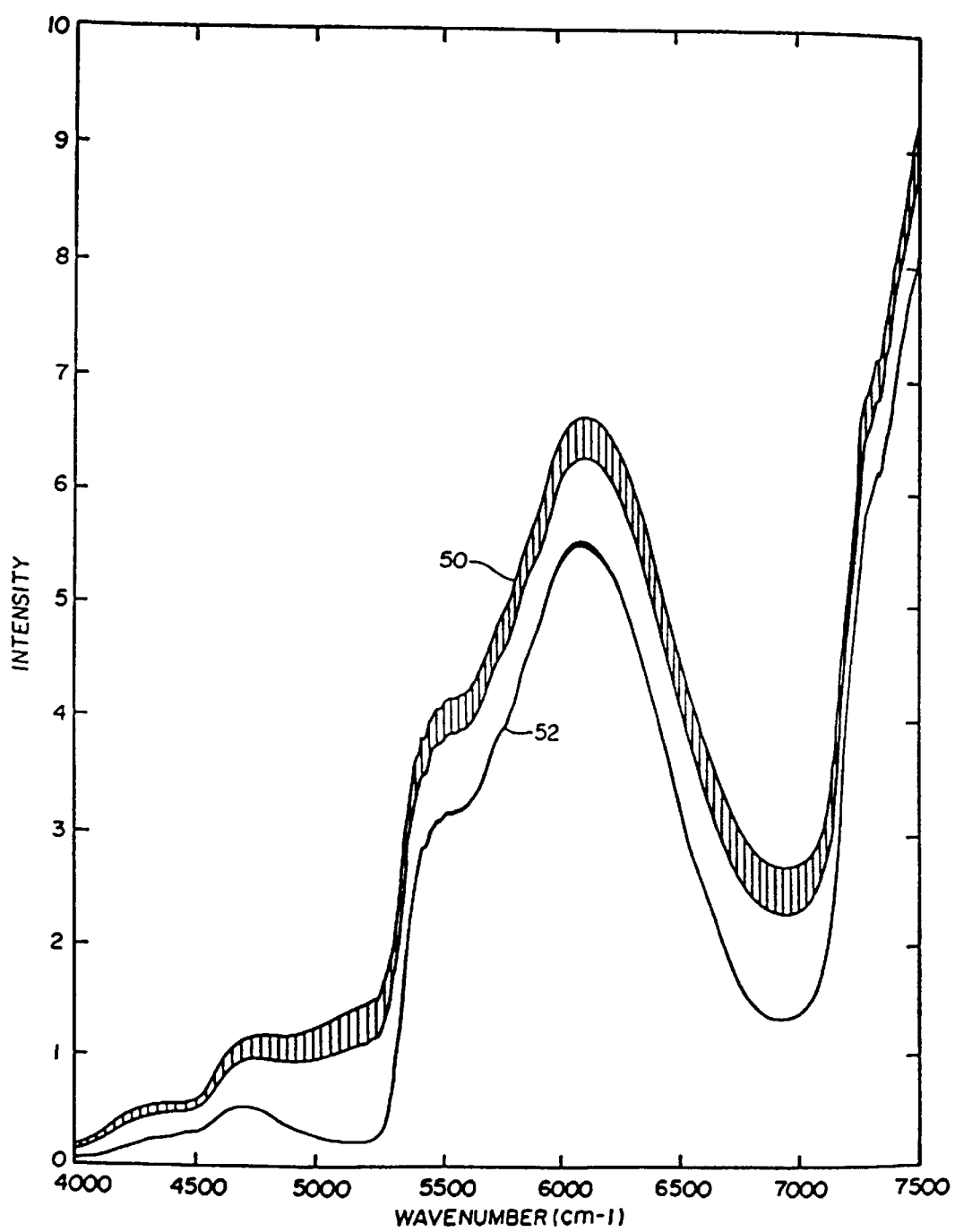
FIG. 3 is a graphical representation of experimental data showing the improvement in accuracy and repeatability of a sensor coupled to the skin via an index-matching medium.

In practicing the present invention, the tissue spectral data is determined by measuring the light intensity received by the output sensor at the various wavelengths which give indications of the absorption at such wavelengths of the infrared energy as a function of the composition of the tissue sample. As is well known in the art, a spectrum analyzer 30 of the present invention is able to convert the intensity of the infrared energy incident on the detector into a proportional amplitude of voltage. In this way, an output spectrum is defined for the tissue under analysis. Experimental results documenting the improvements associated with the above-identified method for obtaining a tissue spectral data are documented in FIG. 3. The top trace, labeled 50, shows the result obtained when sampling in the previously described mode in the absence of an index-matching medium. In the bottom trace, labeled 52, 100 microliters of chlorotrifuoro-ethylene polymer was applied to the surface of the input and output device prior to placing the arm. First, each of the lines drawn, 50 and 52, are each comprised of multiple spectra. With the index-matching fluid, all of the spectra overlay each other quite closely. This is a good indication that the interface is quite stable. Without the index-matching medium, the interface is extremely unstable and it is clear that the data at a particular wavelength would not be particularly accurate when dealing with small changes in concentration of specific constituents that would be indicative of an individual's identity.

Once accurate and repeatable spectral data for tissue analysis is acquired, the second key element of the present invention is to define a methodology for training the device or instrument to identify spectral features or combinations of features that are unique for that particular individual and then to compare the database's spectral data and its unique features to new spectral data from supposedly the same individual to determine whether or not the spectral data in fact came from the same individual.

Figure 5:
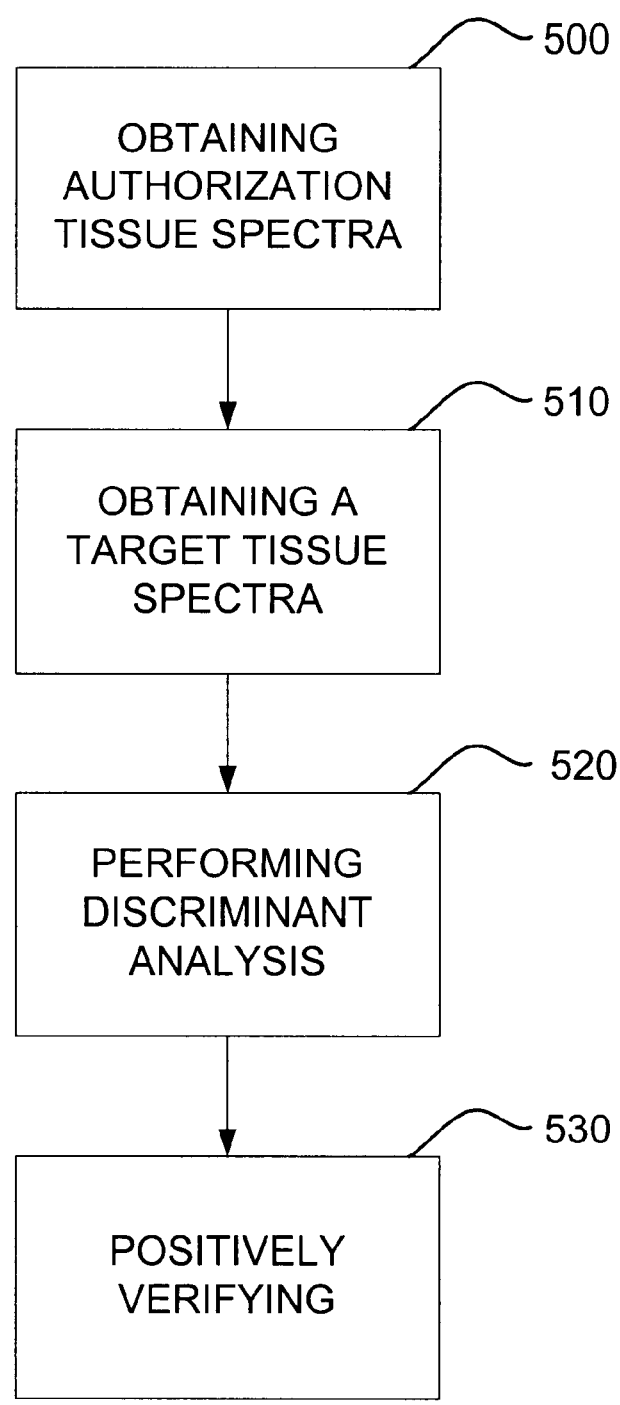
FIG. 5 depicts an alternate identification procedure using near-infrared tissue analysis.

In a preferred method as represented in FIG. 5, the verification task is implemented when a person seeks to perform an operation for which there are a limited number of people authorized (e.g., perform a spectroscopic measurement, gain entry into a room, achieve control over an interlocked vehicle or piece of machinery, etc.). The person's NIR spectral data 500 is used for verification of the person's identity. In this preferred method, the person uses a spectroscopic measurement device to collect one or more tissue spectra 510. Before, during, or after the measurement, the person also states who they are (e.g. "person X") by some means (personal ID number, name, badge, etc.). The verification task is then the confirmation 530 that the person is who they stated by comparison of the near-infrared spectrum with one or more previously recorded and verified spectra from person X. Equivalently, if the verification task is associated with an operation for which only a single person is authorized, then the task simplifies to an assurance that the sole authorized individual is attempting the operation.

In analyzing the data 520, all preferred implementations of the proposed verification methodology generate a difference spectrum, D(v), using the spectrum just collected from the person wishing authorization, V(v), and the prestored authorized spectrum, A(v), or spectra corresponding to the person whose identification was stated:

$$D(v)=V(v)-A(v), \quad \text{Equation 2}$$

where v is a variable designating the spectral frequency or wavelength, and D, V, A are spectral values in absorbance units or some related quantities. Alternatively, D, V, and A could be spectral intensity values, and the "difference" operation becomes an element-by-element ratio:

$$D(v)=V(v)/A(v) \quad \text{Equation 3}$$

Other mathematical operations of a similar nature would also be possible to use for this application.

Figure 6:
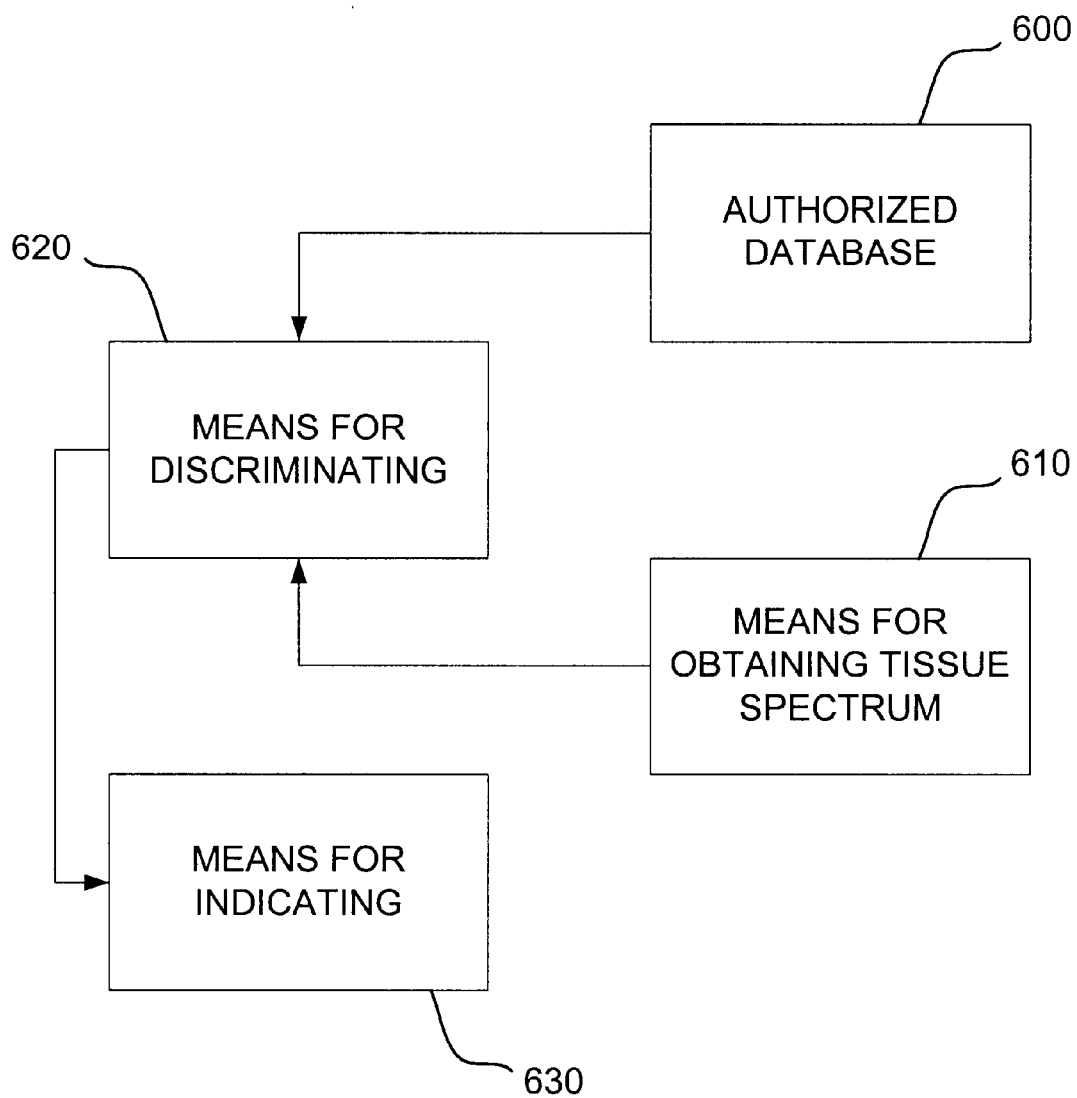
FIG. 6 is a functional diagram of the identification system.

The other key element of a preferred verification method as shown in FIG. 6 is a spectral difference database 600 that was developed using the same mathematical operation as used for generating D(v). The spectral differences (or ratio, etc.) in the spectral difference database are preferably formed from one or more people measured multiple times each 610. For robustness, the sampling of an individual person should span expected changes in the person's physiology, expected changes in or across the spectroscopic measurement devices, and changes in the measurement environment. In one preferred embodiment, spectral differences can be generated in a multitude of combinations of spectra from a given person, but should never be formed using spectra from different people. By filling the database with intra-patient difference spectra, typical inter-patient spectral differences are removed, and the resulting database contains only intrapatient spectral features as well as instrumental and environmental effects.

The verification task is accomplished through determining if the spectral difference, D(v), is consistent with the spectral difference database 600 for the individual. If the identification that the person stated is accurate, the resulting difference spectrum, D(v), will contain only intra-patient spectral features 620, and thus, be consistent with the database. Conversely, if the identification is not accurate, D(v) will contain inter-patient spectral features and be incompatible with the intra-patient spectral difference database for the individual, indicating that the verification failed 630.

Figure 7:
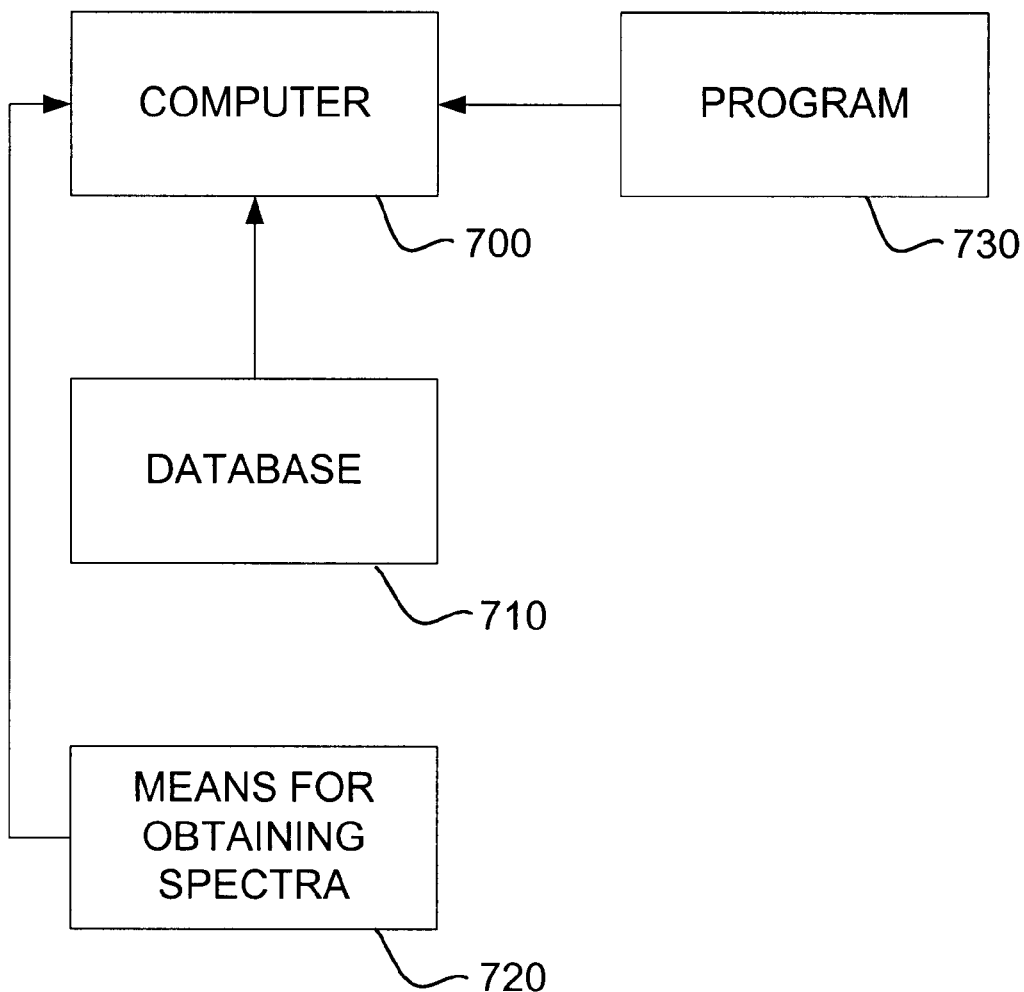
FIG. 7 is a block diagram representing the configuration of the system.

As shown in FIG. 7, consistency with the database 710 can be ascertained in a variety of ways. In preferred methods discriminant analysis techniques 720 incorporated in programs 730 of a computer 700 are used. These methods rely upon establishing the underlying spectral shapes (factors, loading vectors, eigenvectors, latent variables, etc.) in the spectral database, and then using standard outlier methodologies (spectral F ratios, Mahalanobis distances, Eucliden distances, etc.) to determine the consistency of D(v) with the database. The underlying spectral shapes can be generated by multiple means as disclosed herein. First, the underlying spectral shapes can be generated based upon simple spectral decompositions (eigen analysis, Fourier analysis, etc.).

The second method of generating underlying spectral shapes relates to the development of a generic model as described in co-pending U.S. Pat. No. 6,157,041 filed on even-date herewith, entitled "Methods and Apparatus for Tailoring Spectroscopic Calibration Models," the disclosure of which is incorporated by reference. In this application, the underlying spectral shapes are generated through a calibration procedure performed on intra-patient spectral features. The calibration is based upon measured analyte concentration features.

In the third method the underlying spectral shapes can be generated by the development of a calibration based upon simulated constituent variation. The simulated constituent variation can model the variation introduced by real analyte variation or can be simply be an artificial spectroscopic variation. In either situation the variation must be added in a manner that allows calibration development. For example the spectroscopic variation introduced by changing alcohol concentration can artificially be added onto the data in a manner consistent with Beer's law. Results from several different calibrations and corresponding verification results may be able to be combined to enhance the accuracy of the verification.

It is recognized that other means of classifying whether the spectral difference D(v), is or is not consistent with the database would be applicable to the verification method of the present invention. These methods could be used either in conjunction with, or in lieu of the aforementioned techniques.

Many variations in the methodology are possible within the scope of the present invention. In one embodiment, the entire spectra is stored at substantially even wavelength intervals. In another embodiment, only preselected wavelengths of likely interest are recorded. In yet another embodiment, the spectral data are analyzed and stored as parameters capable of substantially regenerating the various spectra. In this later embodiment, measurements at specific wavelengths outside of the parameters are not stored. The verified spectra can be stored in a database. In one embodiment, a number of spectra are obtained at one sitting and used to populate the verified spectra database. In another embodiment, spectra are obtained over several sittings for an individual.

As previously stated, spectral differences or distances can be obtained by performing calculations on different measurements taken at the same wavelength for the same individual. Variations in defining the spectral difference are possible. For the purpose of illustrating the invention consider first the case of measurement samples taken at a single wavelength. The spectral difference can take the form of a statistical analysis of the sample population, such as a mean measurement value and the standard deviation about the mean relative to a new spectral value at that wavelength. Various wavelengths can be evaluated in an attempt to maximize or minimize the standard deviation for the sample population. It may be desirable to select a wavelength to minimize the variation for that wavelength for samples taken for a single individual. At the same time, it is desirable to select a wavelength that varies inter-person, to allow for distinguishing or discriminating between the verified person and an impostor. For example, a wavelength that did not vary intra-person would not be useful for discrimination between persons. At the same time, it is desirable to select a wavelength that does not also vary a great deal between measurements for the same individual, as the intra-person differences can swamp the inter-person differences.

In the simple, single wavelength case discussed above, a wavelength could be selected that maximized inter-person spectral differences while minimizing intra-person spectral differences. In this one-dimensional example, a wavelength could be selected that tended to cluster the measurements for each individual tightly about a single point along an axis, while spreading these tight clusters along the axis for the numerous individuals. When a target sample is introduced, the measurement taken can be compared with the cluster of values for the individual for that purported identity. A threshold can be established for each cluster of values for a verified individual. For example, a threshold could be set at two standard deviations for the sample population, with any measurements falling outside of this range being rejected, and the target individual verification refused.

From the above simplified single wavelength example, the theory of analyzing the spectral data can be expanded. In a two-wavelength example, two wavelengths could be selected and the two wavelength measurements plotted against each other as X-Y coordinates in a two-dimensional plot in a plane. The two-dimensional plot would preferably show a series of clusters widely separated from each other. A threshold can be established for each cluster, for example, using a probability distribution function. The measurement values from a target individual could be analyzed for membership within the sample population, to a certain probability. In one example, membership is confirmed if the target measurement falls within a 99% probability threshold. In another example, the geometric center of the cluster is calculated and stored. The two wavelength measurements taken for an individual could then be plotted, and the spectral distance in two-dimensional space from the cluster center determined. The verification in this example is based on whether the data point for the target individual is judged to be within or without the cluster.

Similarly, a three-wavelength example of the application of this analysis can be envisioned, represented by clusters of data points being plotted in three-dimensional space, and the geometric distance of a target point from a cluster being determined. By extension, ten wavelengths could be selected and the distance of a target point from a cluster calculated in ten-dimensional space. While not as easily envisioned, multiple wavelengths are used in preferred embodiments. In a preferred embodiment, factors, or combinations of measurements taken at a number of wavelengths, are used to simplify analysis, and, at lower dimensions, human visualization.

In an alternative method, functions are used to preprocess spectral measurement values and the resulting function value used rather than the direct measurement. For example, measurement values taken at two wavelengths may be observed to vary up and down, opposite from one another, for an individual, but the average or total of these two values may be seen to be remain constant for that individual. In this example, a plot of the two measurements against each other from several sittings could show a cluster about a line segment having negative slope. A one-dimensional plot of the total or average would show a tight cluster about a single point. In this way, multiple wavelengths may be preprocessed with functions to result in a single value, and the single value used in place of the direct measurements.

In another alternative method, measurements are used to determine an analyte concentration for an individual, and the analyte concentrations used in place of some direct measurements. In this method, multiple tissue spectra and calibration blood samples are taken for a person having a known identity. The calibration samples are used to generate a function that can receive a tissue spectra as input, and output an analyte concentration. A single value can thus be used in place of the multiple wavelength measurements. In use, the purported identity of a target individual is used to preprocess the tissue spectra and arrive at an analyte concentration value.

Selection of which wavelengths to use is important. One method of selecting wavelengths is discussed in U.S. Pat. No. 5,435,309. In one method, wavelengths of interest are selected a priori and used for all samples. In another method, the measurements are periodically used to recalculate inter-person and intra-person differences. The addition of new otherwise closely clustered or even overlapping, individuals into an authorization database can be remedied by choosing different wavelengths, or different functions operating upon these wavelengths.

In use, tissue spectral data can be taken from forearm undersides of individuals, as previously described. The tissue spectral data can then be stored in a computer database. In general, either before or after storage, the underlying spectral shapes and properties such as factors, loading vectors, eigenvectors, and latent variables can be established. Standard outlier methodologies such as spectral F ratios, Mahalanobis distances, and Euclidean distances can be used to determine the consistency of the target spectrum with the spectral database for the person with the purported identity.

In one method, after a sufficient number of spectra have been collected, the database is operated upon by software and discriminant analysis performed on the data, generating the appropriate factors. Discriminant analysis is performed in this method to generate factors useful in clustering the intra-person data points together, while separating the intra-person clusters at a large inter-person distance apart. Examples of discriminant analysis methods useful in conjunction with the present invention include linear discriminant analysis and non-linear discriminant analysis.

Figure 4:
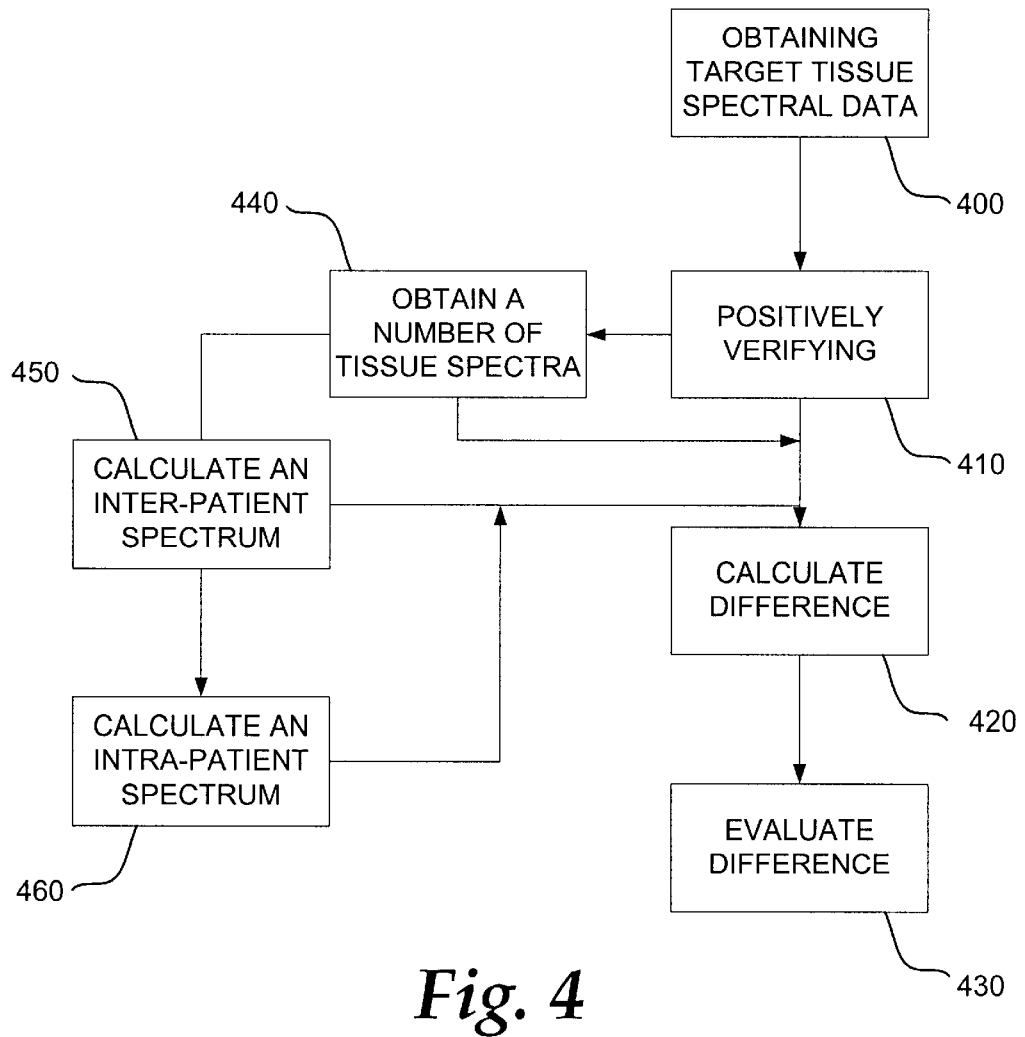
FIG. 4 is a block diagram describing an identification procedure using near-infrared tissue analysis.

In one method depicted in FIG. 4, when identity verification is desired, a tissue spectrum 400 and purported identity are obtained 440 from the target individual. The tissue spectrum is calculated 460 to generate the same factors used to cluster the calculated datapoints 450 in the spectral database. The spectral difference 420 between the target spectrum and the database spectra are calculated. One calculation measures the Mahalanobis distance between the target spectrum and the database spectra for the purported identity. If the distance is less than a threshold distance, then the purported identity can be positively verified 410. Another spectral difference includes computing a spectral residual, or difference spectrum between the target spectrum and a cumulative spectrum, for the purported individual from the database. In evaluating 430 the spectral residual, the identity can be positively identified if the residual is less than a preset threshold. In one method, both the spectral residual and a difference, such as the Mahalanobis distance, must be below their respective thresholds before identity is positively established. In one method, threshold values were set for both spectral distance and spectral residual magnitude to include 99% of the database spectra. In another method, threshold values were set for both spectral distance and spectral residual magnitude to include 95% of the database spectra.

EXPERIMENTAL RESULTS

An experiment was conducted to determine the viability of utilizing the methodology disclosed herein to verify the identification of an individual. The instrumentation utilized was a near infrared Fourier transfer spectrophotometer manufactured by Perkin Elmer. The specific model used as a Perkin Elmer 2000. The sampling of the human tissue was done on the volar side of the forearm. The optical sampling device was a fiber optic sampling device which had separate fibers for launching light into the tissue and fibers for collecting the light exiting the tissue. An index matching fluid was placed between the arm and the fiber optic sampling head. The resulting intensity spectra were converted into absorbance spectra and scaled by a vector wavelength. Spectra were recorded and subsequently processed in the wavelength range of 4,200 to 7,200 $cm^{-1}$. The data consisted of sitting average spectra (5 samples per sitting) measured for 288 different people. Each were measured for a single sitting sometime within a 5 week time span. As well, there were three patients measured for multiple sittings over the same 5 week span (nominally 10 times).

The framework for the investigation assumed a calibration model, a spectral database consisting of spectra from a large number of individuals against whom matching was performed, and a spectrum from an unknown individual (target spectrum). The verification task was to properly identify the target spectrum as either the specified patient or to determine that the patient did not properly identify himself.

The discrimination method applied in this case relied on Mahalanobis distance and the spectral residual magnitude that were generated when a difference spectrum was presented to the calibration model. The spectral difference was formed between the target spectrum and a test spectrum in the database. If the value of the Mahalanobis distance and the spectral residual for a given spectral difference pair were both below a prescribed level, the two spectra were determined to have come from the same individual. If one or both metrics were greater than their respective thresholds, the determination was made that the two spectra came from different individuals.

Thresholds for the two metrics were set by examining the respective cumulative distribution functions for the full-model calibration data. Two threshold values were used for this investigation: one pair that each encompassed 99% of the calibration data ("lenient") and one pair such that each encompassed only 95% of the calibration data ("stringent").

The false positive error rate was examined by using the 288 individual patient spectra in a round-robin fashion. Each was pulled out of the database and an evaluation made of how many of the remaining people in the database matched this spectrum at each of the two similarity thresholds. The false negative error rate was examined by looking at the degree of matching observed between sittings of the same patient (performed for each of the three repeat patients).

When the threshold values were set to the more lenient threshold (99%), the round-robin results showed the number of "matches" that occurred when each of the 288 patients is pulled out from the spectral library and evaluated relative to the remaining 287 patient spectra. On average, each patient matches 0.5 of another patient within this database, yielding a false positive rate of 0.17%. This is the error rate that occurs when a patient not in the database incorrectly specifies that he is one of the library patients and the measurement confirms this.

In a subsequent test, one of the patients, who was measured repeatedly over the 5 week data collection period, was compared to all other observation using the same verification methodology described above. Using the lenient threshold, every sitting matches with every other sitting, resulting in a false negative error rate of 0.0%. Results from the other two repeat patients were similar.

When the verification threshold was set to the slightly more stringent standard (95%), the cross-person and same person results showed there were no matches observed across people, resulting in a false positive error rate of 0.0%. The same person, cross-sitting results show a diminished ability to match any one sitting with any other one sitting, leading to a single-sample false negative error rate of greater than 30%. However, if the spectral library consists of multiple samplings of the patient in different physiologic states, the verification results can be greatly improved. In this case, if the spectral library consists of all nine of the remaining samples, then 100% of the time one or more (actually 3 or more) of the spectral library entries match the target spectrum, resulting in a false negative error rate of 0.0%. Results from the other two repeat patients were similar.

The present invention has been disclosed with focus on in-vivo analysis. It is, however, recognized that the present methods and techniques can be used for in-vitro analysis of blood, tissue or fluid samples.

New characteristics and advantages of the invention covered by this document have been set forth in the foregoing description. It will be understood, however, that this disclosure is, in many respects, only illustrative. Changes may be made in details, particularly in matters of shape, size, and arrangement of parts, without exceeding the scope of the invention. The scope of the invention is, of course, defined in the language in which the appended claims are expressed.

What is claimed is:

1. A method for verifying the purported identity of a target individual utilizing a number of authorization tissue spectral data from verified individuals having known identities, said spectral data having a plurality of measurement wavelengths, comprising the steps of:
   obtaining target tissue spectral data from subepidermal tissue of said target individual by applying a plurality of optical wavelengths to the subepidermal tissue and measuring a plurality of wavelengths emanating from the tissue; and
   positively verifying said target individual's purported identity by confirming consistency of a difference calculated between the target tissue spectral data and authorization tissue spectral data with a database having a plurality of intra-patient difference spectra for the target individual.

2. The method for verifying the purported identity of a target individual as recited in claim 1, further evaluating the difference calculated wherein said evaluation is done by a model that identifies between patients' differences.

3. The method for verifying the purported identity of a target individual as recited in claim 1, wherein said differences are processed through a model to determine the significance of identified differences.

4. The method for verifying the purported identity of a target individual as recited in claim 1, wherein said number of verified individuals is equal to one.

5. The method for verifying the purported identity of a target individual as recited in claim 1, wherein said number of verified individuals is greater than one.

6. The method for verifying the purported identity of a target individual as recited in claim 1, further comprising obtaining a number of authorization tissue spectra from an individual, said number of authorization tissue spectra being greater than two.

7. The method for verifying the purported identity of a target individual as recited in claim 1, wherein said target spectrum is added to said authorization spectra after said verification.

8. The method as recited in claim 1, wherein said number of measurement wavelengths is greater than four, further comprising calculating an inter-person spectral distance between said authorized spectra of said verified individuals at said wavelengths, wherein said wavelengths are selected at least in part to maximize said inter-person spectral differences.

9. The method as recited in claim 8, wherein said number of authorization tissue spectra is greater than four, further comprising calculating an intra-person spectral distance between said authorization spectra for an individual at said wavelengths, wherein said wavelengths are selected at least in part to minimize said intra-person spectral differences.

10. The method as recited in claim 1, wherein said tissue spectra include near-infrared wavelengths.

11. The method as recited in claim 10, wherein said tissue spectra includes a substantial spectral contribution from subcutaneous blood.

12. The method recited in claim 1 wherein applying the plurality of optical wavelengths comprises applying a spectral band of the optical wavelengths.

13. A system for verifying the purported identity of a target individual comprising:
   an authorized database including a plurality of intra-patient difference near-infrared tissue spectra for each of a plurality of authorized persons;
   means for obtaining a near-infrared tissue spectrum and purported identity from said target individual by applying a plurality of optical wavelengths to subepidermal tissue of the target individual and measuring a plurality of wavelengths emanating from the tissue;
   means for discriminating between said target individual near-infrared spectrum and said authorized persons near-infrared spectra by confirming consistency of a difference calculated between the target individual near-infrared spectrum and an authorization near-infrared tissue spectrum with the intra-patient difference near-infrared tissue spectra of the authorized database; and
   means for indicating if said target individual purported identity is correct.

14. The system as recited in claim 13, wherein said discriminating means utilizes said target purported identity.

15. The system as recited in claim 13, wherein said means for discrimination includes means for selecting a plurality of said wavelengths, such that spectral differences between said spectra of said authorized persons is maximized.

16. A system for verifying the purported identify of a target individual comprising:
   a computer including an input device and an output device;
   a database including a plurality of intra-patient difference near-infrared tissue spectra for each of a plurality of authorized persons;
   means for obtaining a near-infrared tissue spectrum from said target individual, including a near-infrared radiation source for projecting a plurality of near-infrared optical wavelengths subcutaneously and a near-infrared spectrometer for measuring subcutaneous near-infrared intensity over a plurality of wavelengths; and
   a program running in said computer for discriminating between said target individual near-infrared spectrum and said authorized persons near-infrared spectra by confirming consistency of a difference calculated between the target individual near-infrared tissue spectrum and an authorization near-infrared tissue spectrum with the intra-patient difference near-infrared tissue spectra of the database.

17. The system of claim 16, wherein said means for obtaining a near-infrared tissue spectra includes an input element and an output element coupled to said tissue via an index-matching medium.

18. The system of claim 17, wherein said index-matching medium comprises a chlorofluorocarbon polymer.

19. The system of claim 18, wherein said polymer includes chlorotrifluoroethylene.

20. The system of claim 17, wherein said index-matching medium has a refractive index between 1.30 and 1.45.

21. A system for verifying the purported identity of a target individual comprising:
- an authorized database including a plurality of intra-patient difference near-infrared tissue spectra for each of a plurality of authorized persons;
- an optical source adapted to apply a plurality of optical wavelengths to subepidermal tissue of the target individual;
- a spectrometer adapted to obtain a near-infrared tissue spectrum from the target individual by measuring a plurality of wavelengths emanating from the tissue;
- a comparator adapted to discriminate between the target individual near-infrared spectrum and the authorized persons near-infrared spectra by confirming consistency of a difference calculated between the target individual near-infrared spectrum and an authorization near-infrared tissue spectrum with the intra-patient difference near-infrared tissue spectra of the authorized database; and
- an indicator adapted to indicate if a purported identity of the target individual is correct.

22. The system of claim 21 wherein the optical source and spectrometer are coupled to the tissue via an index-matching medium.

23. The system of claim 22, wherein the index matching medium comprises a chlorofluorocarbon polymer.

24. The system of claim 23, wherein the polymer includes chlorotrifluoroethylene.

* * * * *